Dec. 24, 1968 N. D. POULSEN Plant Pat. 2,850

ROSE PLANT

Filed July 14, 1967

INVENTOR.

NIELS DINES POULSEN

BY Rummler & Snow ATTYS.

United States Patent Office

Plant Pat. 2,850
Patented Dec. 24, 1968

2,850
ROSE PLANT

Niels Dines Poulsen, Kelleriis, Kvistgaard, Denmark, assignor to Amling-De Vor Nurseries, Inc., Livermore, Calif., a corporation of California Filed July 14, 1967, Ser. No. 653,580
1 Claim. (Cl. Plt.—28)

ABSTRACT OF THE DISCLOSURE

A new variety of floribunda rose plant bearing deep red flowers of medium size borne in clusters and having long persistence as cut flowers; the new plant being particularly characterized by its high production by forcing, its more even growth than other red floribundas, and capacity of being forced without going blind.

BACKGROUND OF THE INVENTION

My new variety rose plant originated as a seedling of Pinocchio × Pinocchio (Pinocchio being Plant Patent No. 848), with Elsinore (unpatented) as the pollen parent, and was developed by me in 1958 in the course of a breeding program carried on by me at Kvistgaard, Denmark with the object of producing a red forcing-rose having the quality of Pinocchio. The new plant was observed to have a strong capacity for forcing and more than seven years of testing has demonstrated that my primary objective has been attained. This new variety of red rose plant flowers continuously and profusely, with blooms of medium size, and has been observed to be free of blueing, even in cold weather, and to be substantially uneffected by wet or hot weather. Also, this plant was found to have a much branched and vigorous growth habit, of upright form averaging about 30 to 40 inches in height.

My new variety of red rose plant has been asexually reproduced by me and under my direction at Kvistgaard, Denmark and successive generations, produced by budding and grafting, have shown that the novel characteristics of the new variety are fixed and hold true, in all respects, from generation to generation. Propagation and field testing of this new variety has also been done at Boskoop, Holland and commercial scale propagation is now being done there as well as at Kvistgaard, Denmark.

DESCRIPTION OF THE DRAWINGS

My new variety of rose plant is illustrated in the accompanying photographic drawing in which.

DESCRIPTION OF THE NEW PLANT VARIETY

Figure 1:
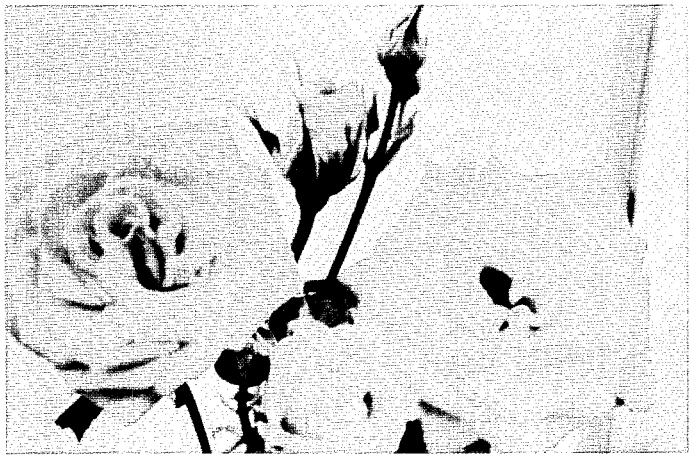
FIG. 1 shows the full open blooms, together with young buds and a partly opened bud.
Figure 2:
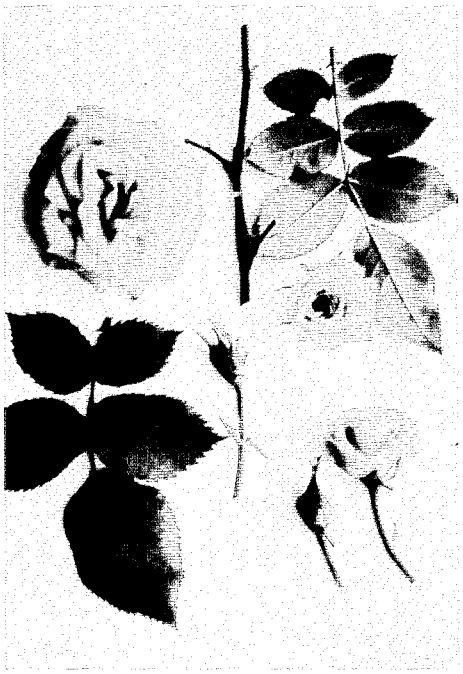
FIGURE 2 shows buds, blooms and foliage to illustrate their form, the true color of the leaves is green but shows bluish in the drawing in order to maintain the true color of red in the blooms.

The following is a detailed description of my new variety of red rose plant, with color designations according to the Horticultural Colour Chart of the British Colour Council.

*The plant*

Origin: Seedling.
Parentage:
*Seed parent.*—Pinocchio × Pinocchio (Pinocchio Plant Parent 484).
*Pollen parent.*—Elsinort (unpatented).
Classification:
*Botanic.*—Hybrid floribunda.
*Commercial.*—Floribunda.
Morm: Bush, upright and much branched.
Height: 30 to 40 inches.

Growth: Vigorous with canes of medium strength.
Foliage: Quantity—abundant.
*Size of leaf.*—Medium.
*Shape of leaf.*—Odd pinnate.
*Leaflets.*—5 and 7 in number, acute-ovate in shape and with serrate margins.
*Texture.*—Leathery with glossy upper surface.
*Color.*—Upper side—green. Under side—green.
*Petioles.*—About 2 to 2½ cm. long.
*Thorns.*—Large, but not hooked. A few spines but no prickles.

*Bud*

Form: Ovoid.
Size: About 3 cm. long and 2½ cm. in diameter.
Bud opens slowly.
Color:
*When sepals first divide.*—820 (HCC).
*When sepals begin to unfurl.*—820.
Sepals: Branched and up-standing. Color: inside—green with whitish hair; outside—green.
Calyx:
*Shape.*—Goblet.
*Size.*—8 to 9 cm. long, 10–12 cm. broad.
*Aspect.*—Smooth; does not split.
Peduncle: 5 to 10 cm. long. Erect and somewhat hairy. Color: green with anthocyanin.

*The flower*

Blooming habit: Continuous and profusely.
Size: Medium, 8 to 9 cm. in diameter.
Borne: In clusters.
Shape: High center. Form does not change with age.
Petalage: About 40, in spiral arrangement.
*Form.*—Obovate.
*Color.*—Outer petal—821/2 to 821/3; white at base. Inside petal—820. Reverse side—820.
*Petaloids.* — Small in size. Number — about 10. Color—red and yellow.
*Texture.*—Leathery. Appearance—shiny.
*Discoloration.*—None.
Peduncle: 5 to 10 cm. long; sturdy and upright. Color—green with anthocyanin.
Fragrance: Little.
Lasting quality: 14 days on plant; 10 to 14 days as a cut flower.
Persistence: Does not hang on and dry.
Disease resistance: This plant has been observed to be resistant to botrytis in an area where this disease is prevalent.

*Genital organs*

Stamens:
*Anthers.*—Very many in number, each about 10 mm. long.
*Filaments.*—7 to 8 mm. long, yellow in color.
Pollen: Yellow in color.
Pistils: Many in number, each about 10 mm. long.
Stigmas: Light yellow in color.
Ovaries: Ordinary—green in color.

*Fruit*

The fruit is fertile and of oblong shape. At maturity the fruit is of a red-yellow color.

My new red rose variety most nearly resembles the floribunda Fire King (Plant Patent 1,758). Differences over Fire King, however are found in that the new variety has a brighter red color in its blooms and does not go blind by forcing as Fire King does. Also the new variety has a better production by forcing, a longer persistence when cut, and a bloom of more even shape than Fire King.

I claim:

1. A new and distinct variety of red-rose plant substantially as herein shown and described, characterized by its capability of being forced without going blind, by its continuous blooming under forcing conditions, by the non-blueing of its flowers, and by the long lasting quality of its blooms on the plant and as cut flowers.

No references cited.

ROBERT E. BAGWILL, *Primary Examiner.*